(12) United States Patent
Zhang et al.

(10) Patent No.: US 11,579,065 B2
(45) Date of Patent: Feb. 14, 2023

(54) METHODS AND SYSTEMS FOR DETERMINING FRACTURE AND MATRIX PERMEABILITY OF A SUBSURFACE FORMATION

(71) Applicant: Saudi Arabian Oil Company, Dhahran (SA)

(72) Inventors: Jilin Jay Zhang, Cypress, TX (US); Hui-Hai Liu, Katy, TX (US); Huangye Chen, Cypress, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 233 days.

(21) Appl. No.: 16/895,177

(22) Filed: Jun. 8, 2020

(65) Prior Publication Data
US 2020/0386664 A1 Dec. 10, 2020

Related U.S. Application Data

(60) Provisional application No. 62/858,132, filed on Jun. 6, 2019.

(51) Int. Cl.
*G01N 15/08* (2006.01)
*E21B 49/02* (2006.01)
*G01N 33/24* (2006.01)

(52) U.S. Cl.
CPC ......... *G01N 15/0826* (2013.01); *E21B 49/02* (2013.01); *G01N 15/0806* (2013.01); *G01N 33/24* (2013.01)

(58) Field of Classification Search
CPC ........... G01N 15/0826; G01N 15/0806; G01N 33/24; E21B 49/02
See application file for complete search history.

(56) References Cited

U.S. PATENT DOCUMENTS 10,416,064 B2  9/2019  Chen et al.
10,502,673 B2  12/2019 Chertov et al.
(Continued)

FOREIGN PATENT DOCUMENTS

CN    103712899 A    4/2014
CN    204177799 U    2/2015
(Continued)

OTHER PUBLICATIONS

Michael Cronin "Core-scale heterogeneity and dual-permeability pore structure in the Barnett Shale". (Year: 2014).*
(Continued)

*Primary Examiner* — Catherine T. Rastovski
*Assistant Examiner* — Kaleria Knox
(74) *Attorney, Agent, or Firm* — Bracewell LLP; Constance G. Rhebergen; Keith R. Derrington (57) ABSTRACT

Methods and systems for determining fracture and matrix permeability of a subsurface formation. The system includes two upstream reservoirs and two downstream reservoirs, and a sample cell connecting to the reservoirs with valves. The sample cell has a confining pressure (CF) from a fluid. A horizontal plug sample with sleeve is placed in a measurement cell with the confining fluid (CF). A pressure gauge is connected to the small upstream reservoir, and a pressure gauge is connected to the small downstream reservoir. The results provide two sets of effective-stress-dependent permeability values (including fracture permeability and matrix permeability, respectively) for characterizing the reservoir properties.

17 Claims, 4 Drawing Sheets

(56) References Cited

U.S. PATENT DOCUMENTS

2018/0364142 A1    12/2018  Georgi et al.
2019/0226970 A1     7/2019  Dusterhoft et al.
2019/0330980 A1    10/2019  Zhu et al.
2019/0353575 A1    11/2019  Clarkson et al.

FOREIGN PATENT DOCUMENTS

CN    107631973 A    1/2018
CN    110296921 A    10/2019

OTHER PUBLICATIONS

International Search Report and Written Opinion for International Application No. PCT/US2020/036452, report dated Sep. 17, 2020; pp. 1-13.

Dicker, A.I. et al.; "A Practical Approach for Determining Permeabiilty From Laboratory Pressure-Pulse Decay Measurements" SPE 17578, SPE International Meeting on Petroleum Engineering, Tianjin, China, Nov. 1-4, 1988; pp. 285-292.

Gan, Zheng et al.; "Fast Pressure-Decay Core Permeability Measurement for Tight Rocks" Petrophysics, vol. 59, No. 5 (Oct. 2018); pp. 606-612.

Luffel, D.L. et al.; "Matrix Permeability Measurement of Gas Productive Shales" SPE 26633, 68th Annual Technical Conference & Exhibition of the Society of Petroleum Engineers, Houston, TX, Oct. 3-6, 1993; pp. 261-270.

* cited by examiner

METHODS AND SYSTEMS FOR DETERMINING FRACTURE AND MATRIX PERMEABILITY OF A SUBSURFACE FORMATION

CROSS-REFERENCE TO RELATED APPLICATIONS

This application claims priority of U.S. Provisional Application No. 62/858,132, titled "METHODS AND SYSTEMS FOR DETERMINING FRACTURE AND MATRIX PERMEABILITY OF A SUBSURFACE FORMATION," which was filed on Jun. 6, 2019, the entire contents of which are incorporated herein by reference.

TECHNICAL FIELD

Embodiments generally relate to methods for measuring permeability of a rock sample, and more specifically relate to methods and systems for determining fracture and matrix permeability a subsurface rock formation.

BACKGROUND

Permeability of a material is a macroscopic property of the material which characterizes the ease with which a fluid can be made to flow through the material by an applied pressure gradient. Thus, permeability is the fluid conductivity of the material. Porosity is the fraction of the bulk volume of the material that is occupied by voids. The total fractional volume of pores in the material can be referred to as total porosity; the fractional volume of only those pores in the material which, under given conditions, are interconnected is known as effective porosity. Permeability measurements of ultra-low permeability (in the range of hundreds of nanoDarcies to 100 milliDarcies) microporous materials present challenges, particularly, in heterogeneous unconventional reservoir rocks.

Unconventional reservoirs such as shales (mudrocks) and coals may exhibit an ultra-low matrix permeability (<0.001 md), challenging conventional laboratory-based methods for permeability measurement. Small-diameter core plugs or crushed-rock samples, combined with unsteady-state methods, are currently favored to reduce measurement times for 'tight' rocks. For core plug analysis, unsteady-state pressure pulse-decay (PDP) or steady-state (SS) methods are commonly employed in commercial laboratories, with the core plug sample subjected to confining stress. Analysis times, particularly for SS methods, may be excessive for ultra-low permeabilities in the nanodarcy range. Another limitation of both PDP and SS experiments applied to core plugs is that they do not represent the boundary conditions typically used to produce hydrocarbons from unconventional reservoirs in the sub-surface through wells.

Rate-transient analysis (RTA) is a technique used to quantitatively analyze production data from wells drilled into unconventional reservoirs to extract reservoir (e.g. permeability, hydrocarbons-in-place) and hydraulic fracture (conductivity, fracture length) properties. Multi-fractured horizontal wells (MFHWs) producing from low-permeability reservoirs commonly exhibit the flow-regime sequence of transient linear flow, where hydrocarbons flow through the reservoir orthogonal to hydraulic fractures or the horizontal well, followed by boundary-dominated flow caused by pressure interference between adjacent hydraulic fractures or wells. Transient linear flow may be analyzed using RTA methods to extract fracture or well-length (if permeability is known); the end of linear flow can be used to estimate permeability of the reservoir, and boundary-dominated flow to estimate hydrocarbons-in-place.

SUMMARY

First, coring and core handling of heterogeneous rock samples can create extensive microcracking. The presence of these microcracks directly affects the permeability measured, and the lower the rock permeability, the greater the effect of the induced microcracks. This effect is most prevalent for laminated, low permeability, organic-rich, mudstones, where the organic to mineral contact and the interfaces associated with the laminated fabric are weak contacts that are prone to part during unloading.

A second challenge in measuring permeability of unconventional formations, low permeability rocks, is heterogeneity. These rocks possess intrinsic variability in texture and composition that results from geologic processes of deposition and diagenesis. As a result, these rocks exhibit a broad distribution of permeabilities. Unfortunately, conventional permeability measurements developed for homogeneous media, have focused on the evaluation of a single representative value of permeability, without accounting for the distribution of permeabilities. The resulting consequences are that the "single permeability" is ill-defined and not necessarily representative of the rock containing the distribution of permeabilities.

A third challenge to measuring permeability, if more conventional fluid flow through plug samples is used for permeability measurements, is the difficulty of flowing through the samples. It can take impractical times to detect measurable flow through samples of standard size (for example 1 to 1.5 inch (25.4 to 38.1 millimeter)) in diameter and 1 to 2 inches (25.4 to 50.8 mm) in length. During these long periods of time, it may simply be impossible to not have small leaks that distort the flow measurements and thereby yield incorrect permeability inferences. The method using crushed fragments of sample tends to be the standard method most often used for measuring permeability in ultra-low permeability rocks. However, the crushed sample fragments' measured permeabilities do not represent the mean value of the whole permeability distribution of the rock before it was crushed, unless a further calibration or correction is made to these measurements.

Methods to measure the matrix permeability of the formation in the laboratory include (1) steady state permeability (SSP) method on core plugs, (2) pulse-decay permeability (PDP) method on core plugs, and (3) pressure decay method on crushed rock samples or the Gas Research Institute (GM) method. The preferred method is the PDP method because the SSP method takes very long time, the measurement results from GM method are very sensitive to the particle size of crushed rock samples, and the GM method itself is limited to the unconfined stress condition.

Regardless of the method, a major concern with the matrix permeability measurement on unconventional shale rock samples is that many samples contain fractures. Unconventional rocks are highly laminated and many weakness planes exist approximately parallel to the lamination due to the orientation of mineral components and distribution of pores and organic matters. Thus the rock samples, when retrieved to the earth surface from the reservoir depth, tend to have more fractures due to the removal of the overburden pressure, and fractures generated through this process are called induced fractures (relative to the in situ fractures, which exist in rocks naturally). If the induced or in-situ fractures are present, the results from the steady-state method and the transient pulse-decay method on the core plug samples would be much greater than the true matrix permeability as it is widely known that the presence of fractures would enlarge the measured permeability of the core sample.

Accordingly, some embodiments relate to methods and systems for measuring both fracture permeability and matrix permeability using a modified PDP method from fractured unconventional source rock samples. The disclosed methods and systems utilize a specially designed hardware to facilitate a new configuration for the measurement of two permeability values in the same experiment run. The results give two sets of effective-stress-dependent permeability (including both fracture permeability and matrix permeability, respectively) for characterizing the reservoir properties.

One example embodiment is a method for determining fracture permeability and matrix permeability of a subsurface formation. The method includes acquiring a sample of the subsurface formation, positioning the sample in a pressure vessel comprising a fluid and a pressure gauge, and applying a constant confining pressure, $P_c$, saturating the sample with a predetermined gas pressure, $P_{sat}$, then applying a pressure pulse $P_{u0}$ to an inlet of the sample, the gas pressure $P_{u0}$ being greater than the saturating pressure, recording the pressure in the upstream and downstream reservoirs as a function of time, $P_u(t)$ and $P_d(t)$ respectively, and determining a matrix permeability of the subsurface formation, $k_m$, using the formula (after the $P_u(t)$ and $P_d(t)$ merge into one curve $P_1(t)$):

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1)$$

where $P_1(t)$ is the pressure in the upstream, downstream and fracture, $t_1$ is the time when both $P_u(t)$ and $P_d(t)$ merge into one curve $P_1(t)$, that is $P_u(t)=P_d(t)=P_1(t)$ when t>t1, $P_\infty$ is the pressure of $P_1$ (t=∞), $f_1$ is a constant, $\phi_m$ is the porosity of the matrix which can be approximated by the total porosity $\phi$, L is the length of the plug sample, and $\varphi_1$ is the first solution of tan $$\tan(\varphi) = -\frac{\varphi}{\omega},$$

where $$\omega = \frac{V_m}{V_e}$$

is the ratio of the pore volume of the rock matrix over the volume of all the connected reservoirs plus the fracture volumes. The core plug analysis in this method is based on a linearized flow of the gas through the sample, and the analysis is performed using an unsteady-state pressure pulse-decay (PDP) method.

The method also include determining fracture permeability using the formula (before $P_u(t)$ and $P_d(t)$ merge into one curve):

$$P_u(t)-P_d(t)=f(\phi,L,A,V_{bulk},c,\mu,V_s,V_u,V_d,k,t)$$

where t is time, k the fracture permeability, $\phi$ the sample's total porosity, L is the sample length, and A is the cross section area of the sample, $V_{bulk}$ the bulk volume of the sample ($V_{bulk}$=L*A; and $$\left(V_{bulk} = L*A; \text{ and } \phi = \frac{V_s}{V_{bulk}}\right),$$

the gas compressibility, $\mu$ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side.

Another example embodiment is a system for determining fracture permeability and matrix permeability of a subsurface formation. The system includes a sample of the subsurface formation placed in a pressure vessel comprising a fluid and a constant confining pressure, $P_c$, saturating the sample with a predetermined gas pressure, $P_{sat}$, then applying a pressure pulse $P_{u0}$ to an inlet of the sample, the gas pressure $P_{u0}$ being greater than the saturating pressure, recording the pressure in the upstream and downstream reservoirs as a function of time, $P_u(t)$ and $P_d(t)$ respectively. The system further includes a processor configured to determining a matrix permeability of the subsurface formation, $k_m$, using the formula (after the $P_u(t)$ and $P_d(t)$ merge into one curve $P_1(t)$):

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1)$$

where $P_1(t)$ is the pressure in the upstream, downstream and fracture, $t_1$ is the time when both $P_u(t)$ and $P_d(t)$ merge into one curve $P_1(t)$, that is $P_u(t)=P_d(t)=P_1(t)$ when t>t1, $P_\infty$ is the pressure of $P_1$ (t=∞), $f_1$ is a constant, $\phi_m$ is the porosity of the matrix which can be approximated by the total porosity $\phi$, L is the length of the plug sample, and $\varphi_1$ is the first solution of $$\tan(\varphi) = -\frac{\varphi}{\omega},$$

where $$\omega = \frac{V_m}{V_e}$$

is the ratio of the pore volume of the rock matrix over the volume of all the connected reservoirs.

The processor further performs the step of determining fracture permeability using the formula:

$$P_u(t)-P_d(t)=f(\phi,L,A,V_{bulk},c,\mu,V_s,V_u,V_d,k,t)$$

where t is time, k the fracture permeability, $\phi$ the sample's total porosity, L is the sample length, and A is the cross section area of the sample, $V_{bulk}$ the bulk volume of the sample $$\left(V_{bulk} = L*A; \text{ and } \phi = \frac{V_s}{V_{bulk}}\right),$$

the gas compressibility, μ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side. The core plug analysis in the system is based on a linearized flow of the gas through the sample, and the analysis is performed using an unsteady-state pressure pulse-decay (PDP) method.

Another example embodiment is a computer readable program for determining fracture permeability and matrix permeability of a subsurface formation. The computer readable program includes computer instructions that when executed by a processor, cause the processor to perform the operations of receiving, from a system including a sample of the subsurface formation placed in a pressure vessel comprising a fluid and a constant confining pressure, $P_c$, saturating the sample with a predetermined gas pressure, $P_{sat}$, then applying a pressure pulse $P_{u0}$ to an inlet of the sample, the gas pressure $P_{u0}$ being greater than the saturating pressure, recording the pressure in the upstream and downstream reservoirs as a function of time, $P_u(t)$ and $P_d(t)$ respectively. The instructions further includes computer code that cause the processor to determine a matrix permeability of the subsurface formation, $k_m$, using the formula (after the $P_u(t)$ and $P_d(t)$ merge into one curve $P_1(t)$):

$$\ln\left(\frac{P_1(t)-P_\infty}{P_1(t_1)-P_\infty}\right) = \ln(f_1) - \varphi_1^2 \frac{4k_m}{c\mu\phi_m L^2}(t-t_1)$$

where $P_1(t)$ is the pressure in the upstream, downstream and fracture, $t_1$ is the time when both $P_u(t)$ and $P_d(t)$ merge into one curve $P_1(t)$, that is $P_u(t)=P_d(t)=P_1(t)$ when t>t1, $P_\infty$ is the pressure of $P_1$ (t=∞), $f_1$ is a constant, $\phi_m$ is the porosity of the matrix which can be approximated by the total porosity $\phi$, L is the length of the plug sample, and $\varphi_1$ is the first solution of $$\tan(\varphi) = -\frac{\varphi}{\omega},$$

where $$\omega = \frac{V_m}{V_e}$$

is the ratio of the pore volume of the rock matrix over the volume of all the connected reservoirs.

The instructions further includes computer code that cause the processor to determine fracture permeability using the formula:

$$P_u(t)-P_d(t)=f(\phi,L,A,V_{bulk},c,\mu,V_s,V_u,V_d,k,t)$$

where t is time, k the fracture permeability, φ the sample's total porosity, L is the sample length, and A is the cross section area of the sample, $V_{bulk}$ the bulk volume of the sample $$\left(V_{bulk} = L * A; \text{ and } \phi = \frac{V_s}{V_{bulk}}\right),$$

the gas compressibility, μ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side. The core plug analysis in the system is based on a linearized flow of the gas through the sample, and the analysis is performed using an unsteady-state pressure pulse-decay (PDP) method.

BRIEF DESCRIPTION OF THE DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

For simplicity and clarity of illustration, the drawing figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of the various embodiments. Like reference numerals refer to like elements throughout the specification.

DETAILED DESCRIPTION

The methods and systems of the present disclosure will now be described more fully with reference to the accompanying drawings in which embodiments are shown. The methods and systems of the present disclosure may be in many different forms and should not be construed as limited to the illustrated embodiments set forth here; rather, these embodiments are provided so that this disclosure will be thorough and complete, and will fully convey its scope to those skilled in the art.

Figure 1:
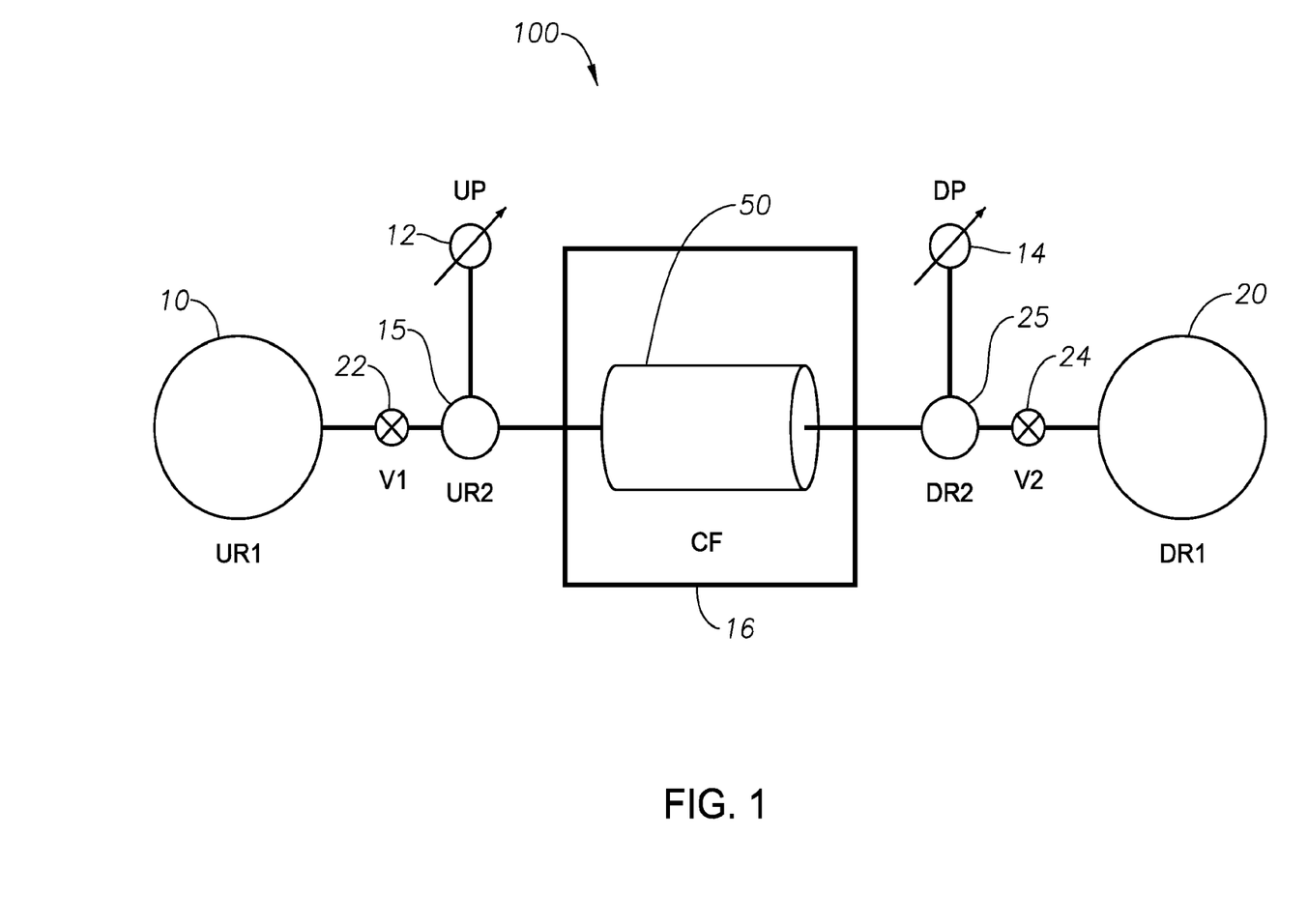
FIG. 1 illustrates an example system for determining fracture and matrix permeability of a subsurface formation, according to one example embodiment of the disclosure.

FIG. 1 illustrates an example system 100 for determining fracture permeability and matrix permeability of a subsurface formation, according to one example embodiment of the disclosure. The system 100 may include two upstream reservoirs 10, 15, two downstream reservoirs 20, 25, and a sample cell 16 connecting to the reservoirs with valves 22, 24. The sample cell 16 has a confining pressure (CF) from a fluid, which may be a gas or a liquid. The pressure can be monitored using one or more pressure gauges and recorded.

More specifically on the upstream side, the system 100 may comprise two gas reservoirs UR1 (10) and UR2 (15) where UR1 is larger than UR2. A similar arrangement is made on the downstream side such that the system 100 includes two gas reservoirs DR1 (20) and DR2 (25) where DR1 is larger than DR2. A horizontal plug sample 50 with sleeve is placed in a measurement cell 16 with the confining fluid (CF). A pressure gauge UP (12) is connected to the small upstream reservoir 15, and a pressure gauge DP (14) is connected to the small downstream reservoir 15, for measuring and recording pressure at multiple points in the system.

In some embodiments, the subsurface formation includes at least one of shale, limestone, siltstone, and sandstone. The fluid includes one or more gases including one or more of methane, argon, nitrogen, carbon dioxide, helium, ethane, and propane. The core sample 50 may be fluidly connected to the supply of fluid via opposite ends of the core sample, as shown in FIG. 1. The core holder or measurement cell 16 may be configured to apply to the core sample 50 a pressure of up to about 10,000 psi, or up to about 20,000 psi, for example.

In one embodiment, a core plug sample 50 of unconventional shale rock, normally a horizontal sample plug with the bedding parallel to the axis of the cylindrical shape of a sample 50, is wrapped in layers of plastic and metal sheet and put between two end pieces with metal lines to connect the sample and the gas reservoirs while keeping the sample well-sealed.

Figure 2:
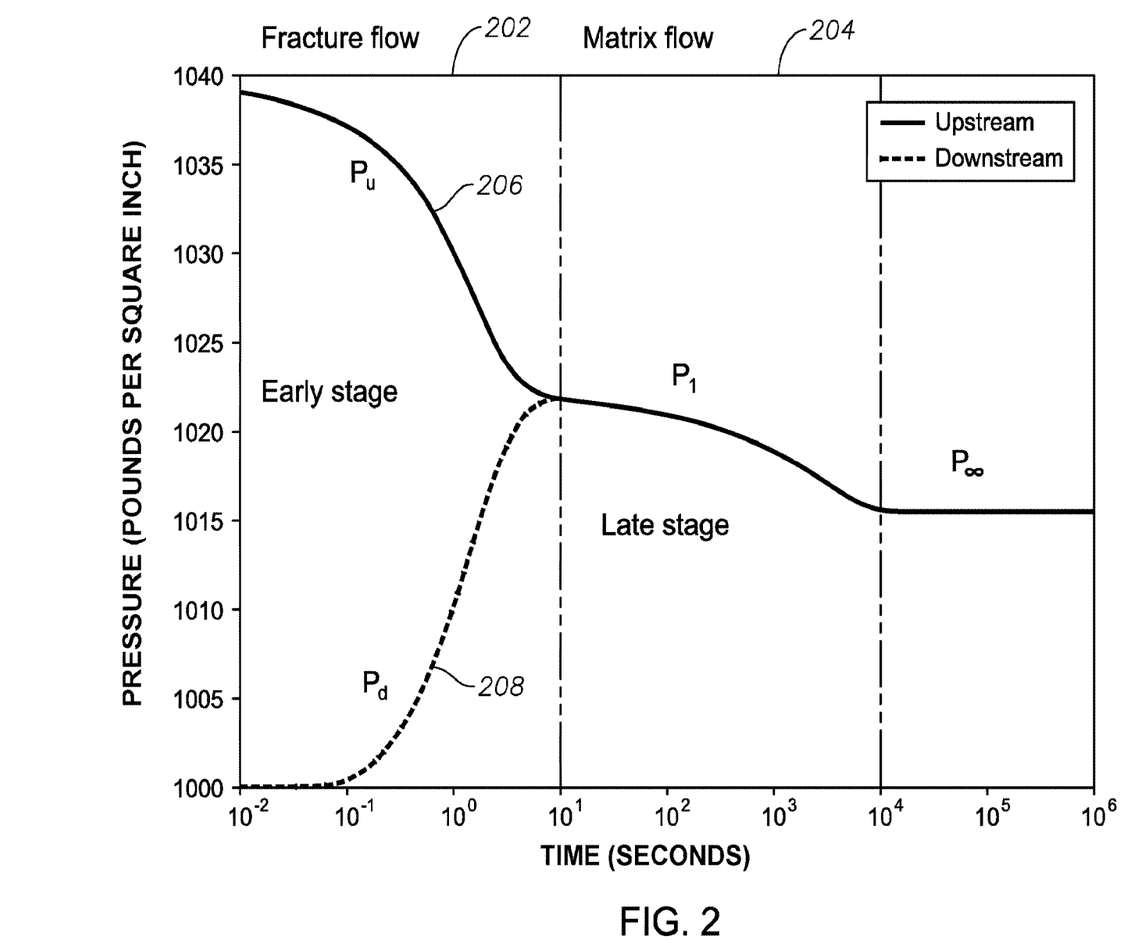
FIG. 2 shows a graphic illustrating two flow regimes in PDP tests, according to one example embodiment of the disclosure.

FIG. 2 shows a graphic illustrating two flow regimes, including fracture flow 202 and matrix flow 204, in PDP tests, according to one example embodiment of the disclosure. The early stage of the pressure pulse decay measurement uses all the reservoirs (upstream reservoirs, UR1, and UR2, where UR2<<UR1; and downstream reservoirs, DR1 and DR2, where DR2<<DR1). The sample 50 is saturated with a selected gas at a predetermined pressure. Next the upstream reservoirs are given a pressure pulse and the gas is allowed to flow through the sample from the upstream side to the downstream side. When the pressures in the upstream and downstream gas reservoirs ($P_u$ 206 and $P_d$ 208, respectively) become practically the same (P1), the late stage experiment starts. The valve (V1) between the two upstream reservoirs is closed. So is the valve (V2) between the two downstream reservoirs. Thus only one pair of small reservoirs (UR2 and DR2) are used for the late stage experiment. The experiment concludes when there is no pressure drop (P∞). The previously described procedure is repeated for a constant pore pressure and different confining stresses values.

Determination of Fracture and Matrix Permeability

FIG. 2 shows a graphic illustrating two flow regimes 202, 204 in PDP tests, according to one example embodiment of the disclosure. The early-stage test is used for determining fracture permeability, and the late stage test is used for determining matrix permeability. The measured pressure signals (as a function of time) are fitted into an analytical equation, which can be written in a general form as:

$$P_u(t) - P_d(t) = f(\phi, L, A, V_{bulk}, c, \mu, V_s, V_u, V_d, k, t) \quad (1)$$

where t is time, k the sample's permeability, $\phi$ the sample's total porosity, L is the sample length, and A is the cross section area of the sample, $V_{bulk}$ the bulk volume of the sample $$\left( V_{bulk} = L^* A; \text{ and } \phi = \frac{V_s}{V_{bulk}} \right),$$

the gas compressibility, μ is the gas viscosity, $V_s$ the pore volume of the sample, Vu is the upstream reservoir volume; $V_d$ is the downstream reservoir volume; Pu(t) pressure of the upstream side, and Pd(t) the pressure downstream side. All variables are in metric units except the dimensionless ones. Some example intermediary variables may be given as follows:

$$t_D = \frac{kt}{c\mu\phi L^2}; a = \frac{V_s}{V_u}; b = \frac{V_s}{V_d}; \tan\theta = \frac{(a+b)\theta}{(\theta^2 - ab)}; \quad (2)$$

$$\Delta P(t_D) = \frac{P_u(t_D) - P_d(t_D)}{P_u(0) - P_d(0)} =$$

$$2\sum_{m=1}^{\infty} \exp(-t_D \theta_m^2) \frac{a(b^2 + \theta_m^2) - (-1)^m b[(a^2 + \theta_m^2)(b^2 + \theta_m^2)]^{0.5}}{\theta_m^4 + \theta_m^2(a + a^2 + b + b^2) + ab(a + b + ab)}$$

where the θ equation has many solutions $\theta_m$ (m=1, 2, 3, . . . ). The left-hand side of Eq. (1) is measured pressure signals and the right-hand side represents a function of both time and related parameters. All these parameters are known except permeability k. Thus Eq. (1) can be solved for determining k, the fracture permeability of the subsurface formation.

During the early stage 202 of the pressure pulse decay measurement on a core sample with fractures, the gas mainly flows within the fractures until the pressures in the upstream 206 and downstream 208 gas reservoirs becomes practically the same value, after which the test is referred as the late stage 204. Once upstream 206 and downstream 208 reservoir pressure becomes the same, the pressure within the system including upstream reservoir, downstream reservoir and fracture reach equilibrium. After this time (referred to as separation point), flow in fractures essentially stops because of zero pressure gradient, but flow still occurs from gas reservoirs into the rock matrix, resulting in further pressure decline, as illustrated in FIG. 2. This late stage 204 pressure decay process is called the matrix flow regime. The pressure data within the matrix flow regime is used to estimate matrix permeability while test results from the early stage 202 is used for estimating the fracture permeability. The traditional PDP methods focus on the early-stage results only. In FIG. 2, the upstream pressure is shown as $P_u$ and the downstream pressure as $P_d$ in the early stage. In the late stage 204, both pressure readings merger into one curve, $P_1$. When the time is long enough, the pressure of the system does not decrease anymore and the reading is marked as $P_\infty$.

The late stage 204 experiment is conducted by switching to much smaller gas reservoirs on both upstream and downstream sides than those used in the early stage, such that the pressure decay in late stage becomes much more obvious and the data are more suitable for the data analysis.

The data analysis for the late-stage experiment is simplified by ignoring the impact of fractures based on the two considerations. Firstly, a source rock sample is anisotropic such that the gas transfer from the fractures into the rock matrix in the direction perpendicular to the fractures (for example across laminations) is negligible compared to the gas flow in the direction parallel to the fractures. Secondly, the length of rock sample is chosen to be considerably small compared to its diameter in our PDP test and thus the area of end-faces (related to gas flow from the two reservoirs to the matrix) is greater than the area of fracture-matrix interface (related to gas flow from the fractures to the matrix).

Therefore, the gas transfer into the sample in the late stage is mainly from the end-faces of a horizontal core plug sample.

The analysis of the test data gives two sets of permeability data corresponding to fractures and the rock matrix, respectively, for different effective stresses (that is the difference between the confining pressure and the pore pressure).

Figure 3A:
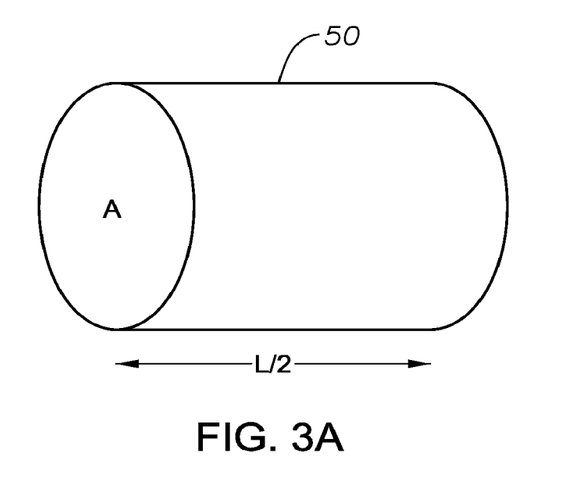
FIG. 3A illustrates a cylindrical core sample used in the systems and methods, according to one or more example embodiments of the disclosure.
Figure 3B:
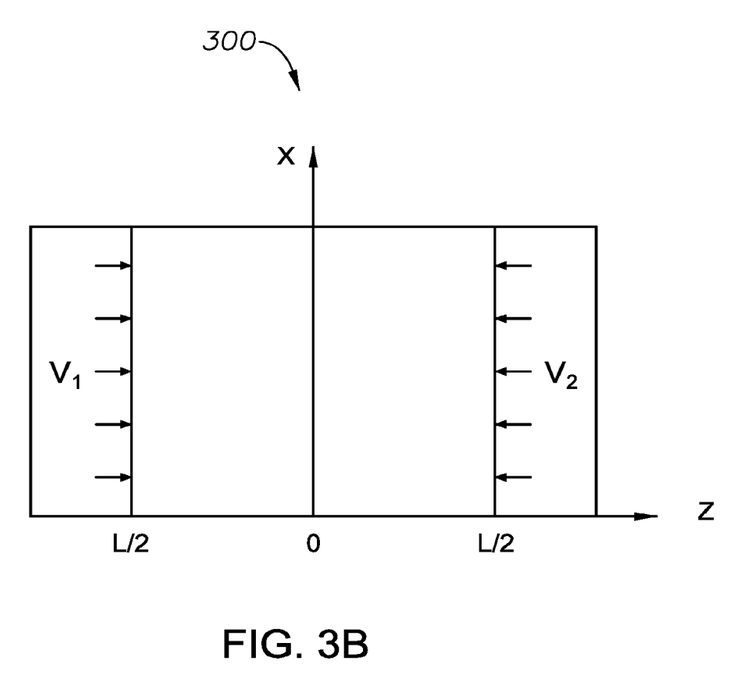
FIG. 3B illustrates a gas flow model for a sample during the matrix flow regime, according to one example embodiment of the disclosure.

FIG. 3A illustrates a cylindrical core sample 50 used in the systems and methods, according to one example embodiment of the disclosure. Sample 50 has a length L/2 and a central axis A-A. FIG. 3B illustrates a gas flow model 300 for a sample 50 during the matrix flow regime, according to one example embodiment of the disclosure. Here, the upstream and downstream are fully equilibrated such that the pressure in both reservoirs are equal and gas still flows from the reservoir to the sample from the end-faces of the sample plug. It should be noted that gas flow from the fracture faces to the matrix is negligible due to two reasons: Firstly, a source rock sample is anisotropic and thus the vertical permeability is significantly less than the horizontal permeability. Secondly, the sample is short such that the area of fracture faces is considerably less than the area of the end faces. Therefore, the gas flow into the sample in the late stage is mainly from the end-faces of a horizontal core plug sample. The details of the analytical derivation are presented in the following paragraphs.

In the late stage the two pressure curves $P_u$ and $P_d$ merge into one. The pressure is denoted as $P_1$ and $t_1$ is the time when both merge. When time is practically long enough, the $P_1$ does not decrease any more. This pressure value is acquired as $P_\infty$. The following equation is used for estimating matrix permeability:

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1) \quad (3)$$

where $f_1$ is a constant, $\phi_m$ is the porosity of the matrix which can be approximated by the total porosity $\phi$, L is the length of the plug sample, and $\varphi_1$ is the first solution of tan $$(\varphi) = -\frac{\varphi}{\omega},$$

where $$\omega = \frac{V_m}{V_e}$$

is the ratio of the pore volume of the rock matrix over the volume of all the connected reservoirs. Matrix permeability, $k_m$, can be estimated using Eq. 3 by fitting the observed data of ln $$\left(\frac{P_1(t) - P_\infty}{P_1(t_1) - P_\infty}\right)$$

versus time. The sum of upstream and downstream volumes can be transformed to an equivalent volume, $V_e$, as:

$$V_e = V_1 + V_2 \quad (4)$$

where $V_1$ and $V_2$ are upstream and downstream volumes (of Reservoir UR2 and DR2), respectively, the volume of fracture is neglected as it is significantly less than the sum of the $V_1$ and $V_2$. During the matrix flow regime, the flow is from both reservoirs to the rock sample, so there is no need to identify upstream or downstream side. Because another set of reservoirs may be used, $V_1$ and $V_2$ are used to differentiate the $V_u$ and $V_d$. Combining Darcy's law and the mass conservation equation, the differential equation for the pressure inside the core sample, P (z, t), as a function of the distance cross the sample length, z, and time, t, when $t > t_1$, is derived as:

$$\frac{\partial^2 P(z,t)}{\partial z^2} = \frac{c\mu\phi_m}{k_m} \frac{\partial P(z,t)}{\partial t}, t > t_1, 0 < z < \frac{L}{2} \quad (5)$$

with the initial conditions:

$$P(z,t_1) = P_1(t_1) z = L/2 \quad (6)$$

$$P(z,t_1) = P(t_1) 0 < z < L/2 \quad (7)$$

and boundary conditions:

$$\frac{\partial P(z,t)}{\partial t} = -\frac{k_m}{c\mu\phi_m} \frac{2A}{V_e} \frac{\partial P(z,t)}{\partial z}, t > t_1, z = \frac{L}{2} \quad (8)$$

$$\frac{\partial P(z,t)}{\partial z} = 0, t > t_1, z = 0 \quad (9)$$

where $t_1$ is the time when the upstream pressure equals to the downstream pressure, A is the inlet surface area of core sample. $P_1(t_1)$ and $P(t_1)$ are the upstream reservoir and matrix pore pressures, respectively, at the $t_1$ time, c and $\mu$ are the compressibility and gas viscosity, respectively, $k_m$ is the matrix porosity, L is the length of the core sample, and $\phi_m$ is the matrix porosity expressed as:

$$\phi_m = \frac{V_m}{V_b} \quad (10)$$

where $V_m$ and $V_b$ are the matrix pore volume and the bulk volume of a rock, respectively. It should be noted that in defining the initial and boundary conditions, symmetry conditions were used such that only the half rock sample is focused on. The dimensionless time for the second-stage process, $\tau$, is defined as:

$$\tau = \frac{4k_m}{c\mu\phi_m L^2}(t - t_1) \quad (11)$$

and dimensionless pressure $P_D$ is defined as:

$$P_D = \frac{P - P_\infty}{P_1(t_1) - P_\infty} \quad (12)$$

$P_\infty$ is pressure of the system when the whole system reaches to the equilibrium (when $t = \infty$), and $\omega$ and r are defined as:

$$\omega = \frac{V_m}{V_e} \quad (13)$$

and

-continued $$r = \frac{z}{L/2} \quad (14)$$

respectively.

With these dimensionless parameters, Eqs. 5 and 8 can be converted to:

$$\frac{\partial^2 P_D(r,\tau)}{\partial r^2} = \frac{\partial P_D(r,\tau)}{\partial \tau}, \tau > 0, 0 < r < 1 \quad (15)$$

$$\omega \frac{\partial P_D(r,\tau)}{\partial r} = -\frac{\partial P_D(r,\tau)}{\partial \tau}, \tau > 0, r = 1 \quad (16)$$

and Eqs. 6 through 9 are transformed to $$P_D(r,\tau) = 1 \quad (17)$$
$$\tau = 0, r = 1$$

$$P_D(r,\tau) = \frac{P(t_1) - P_\infty}{P_1(t_1) - P_\infty}, \tau = 0, 0 < r < 1 \quad (18)$$

$$\frac{\partial P_D(r,\tau)}{\partial r} = 0, \tau > 0, r = 0 \quad (19)$$

Through the Laplace transform and inverse Laplace transform, the analytical solution for the normalized gas pressure of the upstream and downstream reservoirs for the matrix flow regime is obtained:

$$P_D(r=1,t) = \quad (20)$$

$$\frac{P_1(t) - P_\infty}{P_1(t_1) - P_\infty} = 2\sum_{n=1}^{\infty} \exp(-\varphi_n^2 \tau) \left(\frac{1}{\omega + \frac{\varphi_n^2}{\omega} + 1}\right) \left(1 - \frac{1}{\omega+1}\right)^{-1}$$

$\varphi_n$ is the nth root of the following equation:

$$\tan(\varphi) = -\frac{\varphi}{\omega}, \varphi_n > 0 \quad (21)$$

In the case without gas leakage, the matrix permeability can be estimated through the following equation:

$$\ln\left(\frac{P_1(t) - P_\infty}{P_1(t_1) - P_\infty}\right) \approx \ln(f_1) - \varphi_1^2 \tau = \ln(f_1) - \varphi_1^2 \frac{4k_m}{c\mu\phi_m L^2}(t - t_1) \quad (22)$$

where $f_1$ is a constant. Matrix permeability, $k_m$, can be estimated using Eq. 22 by fitting the observed data of ln $$\left(\frac{P_1(t) - P_\infty}{P_1(t_1) - P_\infty}\right)$$

versus time.

Figure 4:
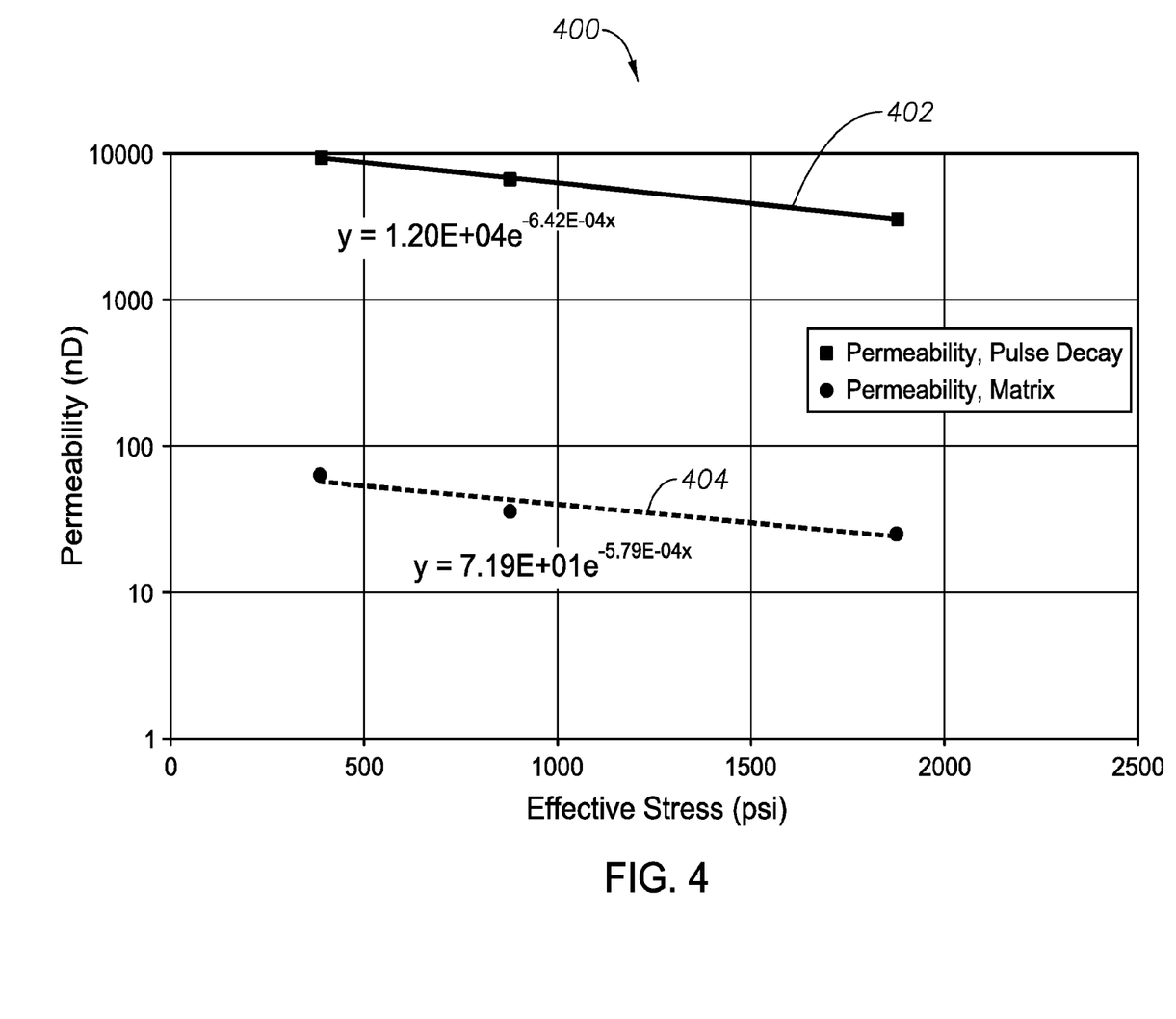
FIG. 4 illustrates test results from a sample showing two sets of permeability values and two permeability-effective-stress relationships, according to one example embodiment of the disclosure.

The previously described systems and methods are used for determining core plug permeability values. FIG. 4 illustrates test results 400 from a sample showing two sets of permeability values (pulse decay and matrix) and two permeability-effective-stress relationships (402, 404), according to one example embodiment of the disclosure.

At each point for a given confining pressure and pore pressure, a fracture permeability (a square) and a matrix permeability (a dot) are acquired. The measured matrix permeability is about two-orders-of-magnitude smaller than the fracture permeability for a given effective stress defined as confining pressure minus pore pressure.

Computer Readable Medium

Another example embodiment is a special purpose computer configured to execute specific computer instructions in a computer program stored in computer readable media. The foregoing process as explained with reference to FIGS. 1-4 can be embodied in computer-readable code. The code can be stored on, for example, a computer readable medium, such as a floppy disk or a USB or a CD-ROM, which may be read by a disk drive, or a magnetic (or other type) hard drive forming part of a general purpose programmable computer. The computer, as known in the art, includes a central processing unit including one or more processors, a user input device such as a keyboard and a user display such as a flat panel display or cathode ray tube display. According to this aspect, the computer readable medium includes logic operable to cause the computer to execute acts as set forth previously and explained with respect to the previous figures. The non-transitory computer-readable medium having computer executable instructions cause a computer to perform the operations of determining a matrix permeability of the subsurface formation, $k_m$, using the formula:

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1) \quad (23)$$

where $f_1$ is a constant, $\phi_m$ is the porosity of the matrix which can be approximated by the total porosity $\phi$, L is the length of the plug sample, and $\varphi_1$ is the first solution of $$\tan(\varphi) = -\frac{\phi}{\omega},$$

where $$\omega = \frac{V_m}{V_e}$$

is the ratio of the pore volume of the rock matrix over the volume of all the connected reservoirs, $V_m$, being the volume of matrix pore space, and $V_e$ the volume of the connected space when the upstream and downstream pressure merge into one. The processor may further be configured to perform the step of determining fracture permeability using the formula:

$$P_u(t) - P_d(t) = f(\phi, L, A, V_{bulk}, c, \mu, V_s, V_u, V_d, k, t) \quad (24)$$

where t is time, k the fracture permeability, $\phi$ the sample's total porosity, L is the sample length, and A is the cross section area of the sample, $V_{bulk}$ the bulk volume of the sample $$\left(V_{bulk} = LA; \text{ and } \phi = \frac{V_s}{V_{bulk}}\right),$$

the gas compressibility, μ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side.

The methods and systems disclosed here measure both the fracture permeability and matrix permeability simultaneously within a single test run. Additionally, the methods and systems disclosed provide both fracture and matrix permeability under many effective pressure conditions, whereas prior art methods do not have the ability to measure matrix permeability under any confining pressure other than zero confining pressure.

In some above embodiments, the subsurface formation includes at least one of shale, limestone, siltstone, and sandstone. The fluid includes one or more gases including one or more of methane, argon, nitrogen, carbon dioxide, helium, ethane, and propane. The core sample may be fluidly connected to the supply of fluid via opposite ends of the core sample. The core holder may be configured to apply to the core sample a pressure of up to about 10,000 psi, or up to about 20,000 psi.

The Specification, which includes the Summary, Brief Description of the Drawings and the Detailed Description, and the appended Claims refer to particular features (including process or method steps) of the disclosure. Those of skill in the art understand that the disclosure includes all possible combinations and uses of particular features described in the Specification. Those of skill in the art understand that the disclosure is not limited to or by the description of embodiments given in the Specification.

Those of skill in the art also understand that the terminology used for describing particular embodiments does not limit the scope or breadth of the disclosure. In interpreting the Specification and appended Claims, all terms should be interpreted in the broadest possible manner consistent with the context of each term. All technical and scientific terms used in the Specification and appended Claims have the same meaning as commonly understood by one of ordinary skill in the art to which this disclosure belongs unless defined otherwise.

As used in the Specification and appended Claims, the singular forms "a," "an," and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

The systems and methods described here are well adapted to carry out the objects and attain the ends and advantages mentioned. While example embodiments of the system and method have been given for purposes of disclosure, numerous changes exist in the details of procedures for accomplishing the desired results. These and other similar modifications may readily suggest themselves to those skilled in the art, and are intended to be encompassed within the spirit of the system and method disclosed here and the scope of the appended claims.

The invention claimed is:

1. A method for determining matrix permeability of a subsurface formation, comprising:

acquiring a sample of the subsurface formation;

positioning the sample in a pressure vessel comprising a fluid and a pressure gauge, and applying a constant confining pressure, $P_u$;

executing a test run which includes applying a predetermined gas pressure, $P_o$, to an inlet of the sample, the gas pressure being greater than the confining pressure; and during the test run, determining a fracture permeability using the formula before the $P_u(t)$ and $P_d(t)$ merge into one curve:

$$P_u(t)-P_d(t)=f(\phi,L,A,V_{bulk},c,\mu,V_s,V_u,V_d,k,t)$$

where t is time, k the fracture permeability, ϕ the sample's total porosity, L is the sample length, and A is the cross section area of the sample, $V_{bulk}$ the bulk volume of the sample $$\left(V_{bulk} = LA; \text{ and } \phi = \frac{V_s}{V_{bulk}}\right),$$

the gas compressibility, μ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side; and during the same test run, determining a matrix permeability of the subsurface formation, $k_m$, using the formula after the $P_u(t)$ and $P_d(t)$ merge into one curve $P_1(t)$:

$$\ln\left(\frac{P_1(t)-P_\infty}{P_1(t_1)-P_\infty}\right) = \ln(f_1) - \varphi_1^2 \frac{4k_m}{c\mu\phi_m L^2}(t-t_1)$$

where $P_1(t)$ is the pressure in the upstream, downstream and fracture, $t_1$ is the time when both $P_u(t)$ and $P_d(t)$ merge into one curve $P_1(t)$, that is $P_u(t)=P_d(t)=P_1(t)$ when t>t1, $P_\infty$ is the pressure of $P_1(t=\infty)$, $f_1$ is a constant, $\phi_m$ is the porosity of the matrix which can be approximated by the total porosity ϕ, L is the length of the plug sample, and $\varphi_1$ is the first solution of $$\tan(\varphi) = -\frac{\phi}{\omega},$$

where $$\omega = \frac{V_m}{V_e}$$

is the ratio of the pore volume of the rock matrix, $V_m$ over the volume of all the connected reservoirs, $V_e$.

2. The method according to claim 1, wherein a first boundary condition comprises:

$$\frac{\partial P(z,t)}{\partial t} = -\frac{k_m}{c\mu\phi_m}\frac{2A}{V_e}\frac{\partial P(z,t)}{\partial z}, t > t_1, z = \frac{L}{2}.$$

3. The method according to claim 1, wherein a second boundary condition comprises:

$$\frac{\partial P(z,t)}{\partial z} = 0, t > t_1, z = 0.$$

4. The method according to claim 1, wherein the subsurface formation comprises at least one of shale, limestone, siltstone, and sandstone.

5. The method according to claim 1, wherein the fluid comprises one or more gases including one or more of methane, argon, nitrogen, carbon dioxide, helium, ethane, and propane.

6. The method according to claim 1, wherein the formation sample is fluidly connected to the supply of fluid via opposite ends of the sample.

7. A system for determining matrix permeability of a subsurface formation, comprising:
  a sample of the subsurface formation placed in a pressure vessel comprising a fluid and a constant confining pressure, $P_c$;
  a upstream and a downstream reservoir for applying a predetermined gas pressure, $P_{sat}$, to saturate the sample;
  a upstream reservoir for applying a predetermined gas pressure pulse, $P_{uo}$, to an inlet of the sample, the gas pressure being greater than the saturation pressure, $P_{sat}$; and
  a processor configured to:
  determine a fracture permeability during a test run of applying the predetermined gas pressure, $P_{sat}$, and predetermined gas pressure pulse, $P_{uo}$, using the formula before the $P_u(t)$ and $P_d(t)$ merge into one curve:

$$P_u(t) - P_d(t) = f(\phi, L, A, V_{bulk}, c, \mu, V_s, V_u, V_d, k, t)$$

where t is time, k the fracture permeability, $\phi$ the sample's total porosity, L is the sample length, and A is the cross section area of the sample, $V_{bulk}$ the bulk volume of the sample $$\left(V_{bulk} = L * A; \text{ and } \phi = \frac{V_s}{V_{bulk}}\right),$$

the gas compressibility, $\mu$ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side; and
  determine a matrix permeability of the subsurface formation, km, during the same test run using the formula (after the $P_u(t)$ and $P_d(t)$ merge into one curve $P_1(t)$):

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1)$$

Where $P_1(t)$ is the pressure in the upstream, downstream and fracture, $t_1$ is the time when both $P_u(t)$ and $P_d(t)$ merge into one curve $P_1(t)$, that is $P_u(t)=P_d(t)=P_1(t)$ when $t>t1$, $P_\infty$ is the pressure of $P_1(t=\infty)$, $f_1$ is a constant, $\phi_m$ is the porosity of the matrix which can be approximated by the total porosity $\phi$, L is the length of the plug sample, and $\varphi_1$ is the first solution of $$\tan(\varphi) = -\frac{\phi}{\omega},$$

where $$\omega = \frac{V_m}{V_e}$$

is the ratio of the pore volume of the rock matrix, $V_m$, over the volume of all the connected reservoirs plus the fracture volumes, $V_e$.

8. The system according to claim 7, wherein a first boundary condition comprises:

$$\frac{\partial P(z,t)}{\partial t} = -\frac{k_m}{c\mu\phi_m}\frac{2A}{V_e}\frac{\partial P(z,t)}{\partial z}, t > t_1, z = \frac{L}{2}.$$

9. The system according to claim 7, wherein a second boundary condition comprises:

$$\frac{\partial P(z,t)}{\partial z} = 0, t > t_1, z = 0.$$

10. The system according to claim 7, wherein the subsurface formation comprises at least one of shale, limestone, siltstone, and sandstone.

11. The system according to claim 7, wherein the fluid comprises one or more gases including one or more of methane, argon, nitrogen, carbon dioxide, helium, ethane, and propane.

12. The system according to claim 7, further comprising a vacuum pump configured to evacuate the formation sample of gas.

13. The system according to claim 7, wherein the formation sample is fluidly connected to the supply of fluid via opposite ends of the sample.

14. The system according to claim 7, wherein the core holder is configured to apply to the formation sample a pressure of up to about 10,000 psi, or up to about 20,000 psi.

15. A computer readable program comprising computer readable instructions that when executed by a processor, the cause the processor to perform the operations of:
  using the processor while performing a test run on a sample of a subsurface formation to determine a fracture permeability of the subsurface formation, using the formula before the $P_u(t)$ and $P_d(t)$ merge into one curve:

$$P_u(t) - P_d(t) = f(\phi, L, A, V_{bulk}, c, \mu, V_s, V_u, V_d, k, t)$$

where t is time, k the fracture permeability, $\phi$ the sample's total porosity, L is the sample length, and A is the cross section area of the sample, $V_{bulk}$ the bulk volume of sample $$\left(V_{bulk} = L * A; \text{ and } \phi = \frac{V_s}{V_{bulk}}\right),$$

the gas compressibility, μ is the gas viscosity, $V_s$ the pore volume of the sample, $V_u$ is the upstream reservoir volume; $V_d$ is the downstream reservoir volume; $P_u(t)$ is the pressure of the upstream side, and $P_d(t)$ is the pressure downstream side; and during the same test run on the sample of a subsurface formation, using the processor to determine a matrix permeability of the subsurface formation, $k_m$, using the formula (after the $P_u(t)$ and $P_d(t)$ merge into one curve $P_1(t)$):

$$\ln\left(\frac{P_1(t) - P_\infty}{P_1(t_1) - P_\infty}\right) = \ln(f_1) - \varphi_1^2 \frac{4k_m}{c\mu\phi_m L^2}(t - t_1)$$

Where $P_1(t)$ is the pressure in the upstream, downstream and fracture, $t_1$ is the time when both $P_u(t)$ and $P_d(t)$ merge into one curve $P_1(t)$, that is $P_u(t) = P_d(t) = P_1(t)$ when t>t1, $P_\infty$ is the pressure of $P_1$ (t=∞), $f_1$ is a constant, $\phi_m$ is the porosity of the matrix which can be approximated by the total porosity φ, L is the length of the plug sample, and $\varphi_1$ is the first solution of $$\tan(\varphi) = -\frac{\varphi}{\omega},$$

where $$\omega = \frac{V_m}{V_e}$$

is the ratio of the pore volume of the rock matrix, $V_m$, over the volume of all the connected reservoirs plus the fracture volumes, $V_e$; where during the test run, the sample of the subsurface formation has been positioned in a pressure vessel comprising a fluid and a pressure gauge;

a constant confining pressure $P_u$ is applied to the sample; and a predetermined gas pressure, $P_o$ is applied to an inlet of the sample, the gas pressure being greater than the confining pressure.

16. The program according to claim 15, wherein a first boundary condition comprises:

$$\frac{\partial P(z,t)}{\partial t} = -\frac{k_m}{c\mu\phi_m}\frac{2A}{V_e}\frac{\partial P(z,t)}{\partial z}, t > t_1, z = \frac{L}{2}.$$

17. The program according to claim 15, wherein a second boundary condition comprises:

$$\frac{\partial P(z,t)}{\partial z} = 0, t > t_1, z = 0.$$

* * * * *